(12) United States Patent
Chen

(10) Patent No.: US 8,038,963 B1
(45) Date of Patent: Oct. 18, 2011

(54) GARMENT BAG

(76) Inventor: Chung-Yang Mike Chen, Irvine, CA (US)

(*) Notice: Subject to any disclaimer, the term of this patent is extended or adjusted under 35 U.S.C. 154(b) by 0 days.

(21) Appl. No.: 12/769,753

(22) Filed: Apr. 29, 2010

(51) Int. Cl.
*A61L 2/20* (2006.01)

(52) U.S. Cl. .................. 422/294; 422/186.07; 422/292; 34/210

(58) Field of Classification Search .......... 422/120, 422/292, 294, 186.07; 34/201
See application file for complete search history.

(56) References Cited

U.S. PATENT DOCUMENTS

| 5,713,137 | A  | * | 2/1998  | Fujita       | 34/106    |
|-----------|----|---|---------|--------------|-----------|
| 5,930,915 | A  | * | 8/1999  | Dhaemers     | 34/511    |
| 6,134,806 | A  | * | 10/2000 | Dhaemers     | 34/404    |
| 6,840,068 | B2 | * | 1/2005  | Pasin et al. | 68/5 C    |
| 2002/0053607 | A1 | * | 5/2002 | Gaaloul et al. | 239/102.2 |
| 2008/0118411 | A1 | * | 5/2008 | D'Arinzo     | 422/186.09 |

* cited by examiner

*Primary Examiner* — Sean E Conley

(74) *Attorney, Agent, or Firm* — Rosenberg, Klein & Lee

(57) ABSTRACT

A garment bag is sleeved over an ozone generator generating ozone therein. The garment bag includes a hollow bag body and an ozone filter unit. The ozone filter unit is disposed on the bag body. When the ozone in the bag body flows to the ozone filter unit, the ozone can be decomposed by the ozone filter unit.

7 Claims, 8 Drawing Sheets

GARMENT BAG

BACKGROUND OF THE INVENTION

1. Field of the Invention

The present invention relates to a garment bag, more particularly to a garment bag sleeved over to an ozone generator.

2. Description of the Prior Art

Some dresses of high cost or value (such as silk, leather, feather dresses and furs) are generally sent to laundry for dry cleaning to prevent damage done onto them. However, it is noted that the dry cleaning fee is relatively high and therefore incurs an extra burden for every person or family.

The dresses or uniforms we generally wear in work or offices are usually contaminated with peculiar smell (unwanted smell), thereby causing discomfort to the wearers. For instance, the dress of a smoker is contaminated with cigarette smell that seldom disperses off and the smell is unbearable for those nearby persons. In the event, high-cost dresses worn by the persons accustomed to smoking are always sent to laundry for dry cleaning, there may occur a great extra expense.

A general method for getting rid of the undesired smell is to dispose a smell remover (including drying agent, desiccating agent, an exsiccator and desiccant) within a clothes wardrobe or cabinet, where the dresses are deodorized by the smell remover. However, since each wardrobe has a considerable space and a relatively large quantity of smell removers must be disposed therein so as to deodorize specific suits of dresses, thereby causing extra expense for purchasing new sets of the smell remover. In addition, majority of the wardrobes have no sealed chamber to prevent leakage of the deodorizing effect, the deodorizing effect produced by the smell remover is decreased due to presence of the gap, which, in turn, causes the user to purchase a new set of smell remover at a predetermined short period of time. In case other electronic deodorizing device, which is relatively expensive when compared to the smell remover, is disposed within the wardrobe to deodorize the dresses, an extra expense will be caused to the user and therefore using electronic deodorizing device is not economized.

SUMMARY OF THE INVENTION

Therefore, in order to solve the above-mentioned drawbacks, it is the object of the present invention is to provide a garment bag. The garment bag is sleeved over an ozone generator generating ozone therein, thereby causing the ozone generator to produce lesser amount of ozone and reducing the risk happened due to leakage of ozone to environment.

A garment bag is provided according to the present invention to connect to an ozone generator, includes a hollow bag body, a seal unit, a zipper structure and a ozone filter unit. The hollow bag body receives ozone generated by the ozone generator. The seal unit is disposed on the bag body and sleeved over the ozone generator. The zipper structure is disposed on the side of the bag body to prevent the ozone leaking from the zipper structure. The ozone filter unit is disposed on the bag body. When the ozone in the bag body flows to the ozone filter unit, the ozone filter unit decomposes part of the ozone.

As explained above, the ozone generator of the present invention generates lesser ozone amount when compared to the prior art to deodorize the dresses. The seal unit and the zipper structure are to prevent leakage of ozone from the garment bag. Moreover, when the ozone with odor molecule flows to the ozone filter unit, them can be decomposed by the ozone filter unit. The dresses will be deodorized effectively and the ozone amount out of the garment bag will correspond with the ozone safety standard, thereby there is no danger caused the health of nearby persons.

BRIEF DESCRIPTION OF THE DRAWINGS

Other features and advantages of this invention will become more apparent in the following detailed description of the preferred embodiments of this invention, with reference to the accompanying drawings, in which.

DETAILED DESCRIPTION OF THE PREFERRED EMBODIMENTS

Figure 1:
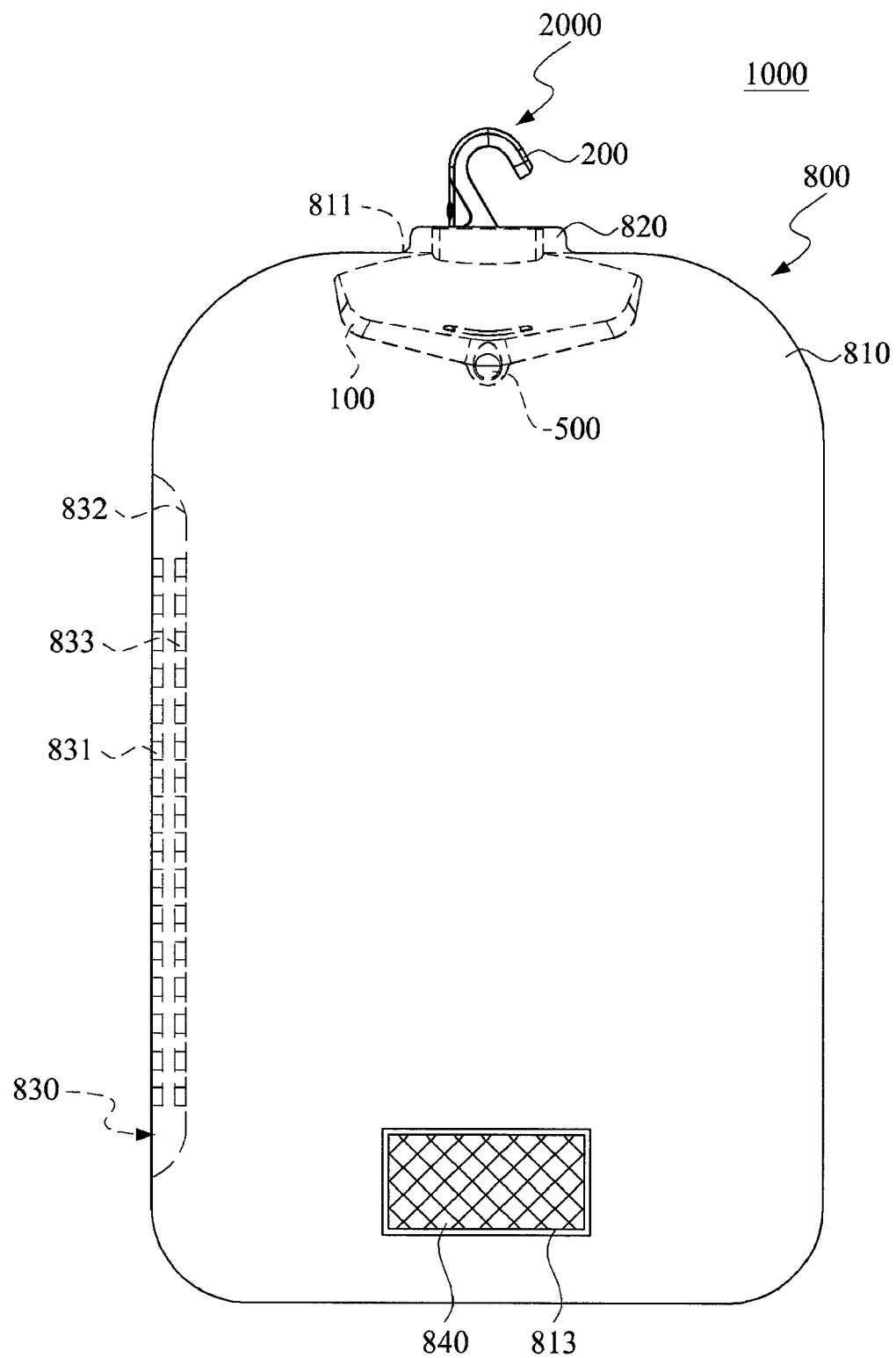
FIG. 1 is a schematic view of the first embodiment of an ozone device of the present invention.

FIG. 1 is a schematic view of the first embodiment of an ozone device of the present invention. As illustrated, the ozone device 1000 accordingly includes an ozone generator 2000 and a garment bag 800. The ozone generator 2000 is capable of generating ozone while the garment bag 800 is connected to the ozone generator 2000 to define a chamber so that dresses can be kept therein.

Figure 7:
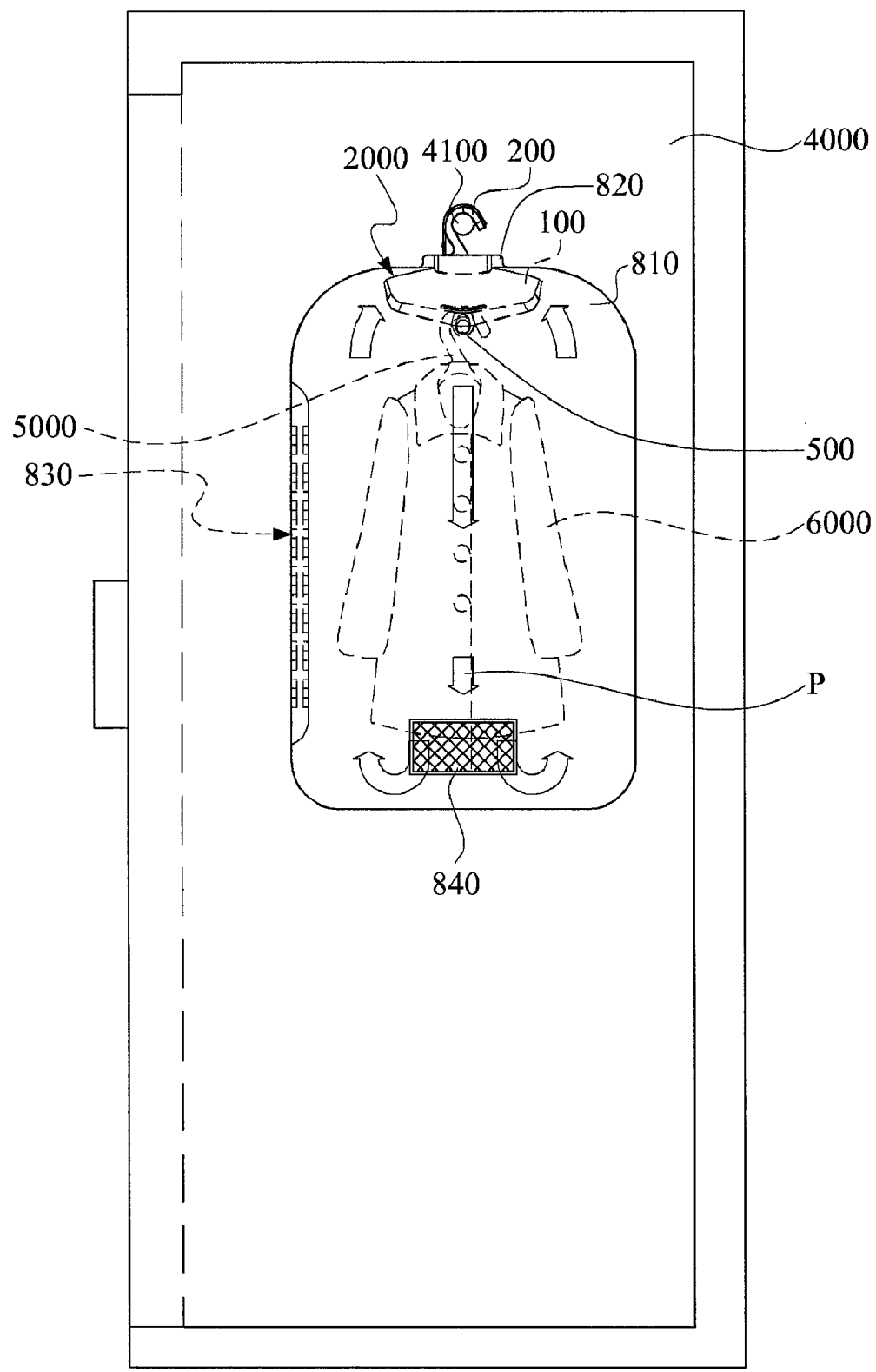
FIG. 7 illustrates how the ozone device of the present invention is used within a wardrobe.

The garment bag 800 further includes a zipper structure 830 for fastening an opening for access into the chamber. The ozone generator 2000 includes a casing 100 for disposing within the garment bag 800, a hanging unit 200 and a suspending rod unit 500. The zipper structure 830 is pulled downward to uncover the opening via which the ozone generator 2000 can be inserted into the garment bag 800 such that the hanging unit 200 projecting outward from a top portion of the garment bag 800 and is adapted to be hung onto a suspension member (as shown in FIG. 7). Under this condition, the garment bag 800 and the casing 100 do not separate and cooperatively define the chamber.

Figure 2:
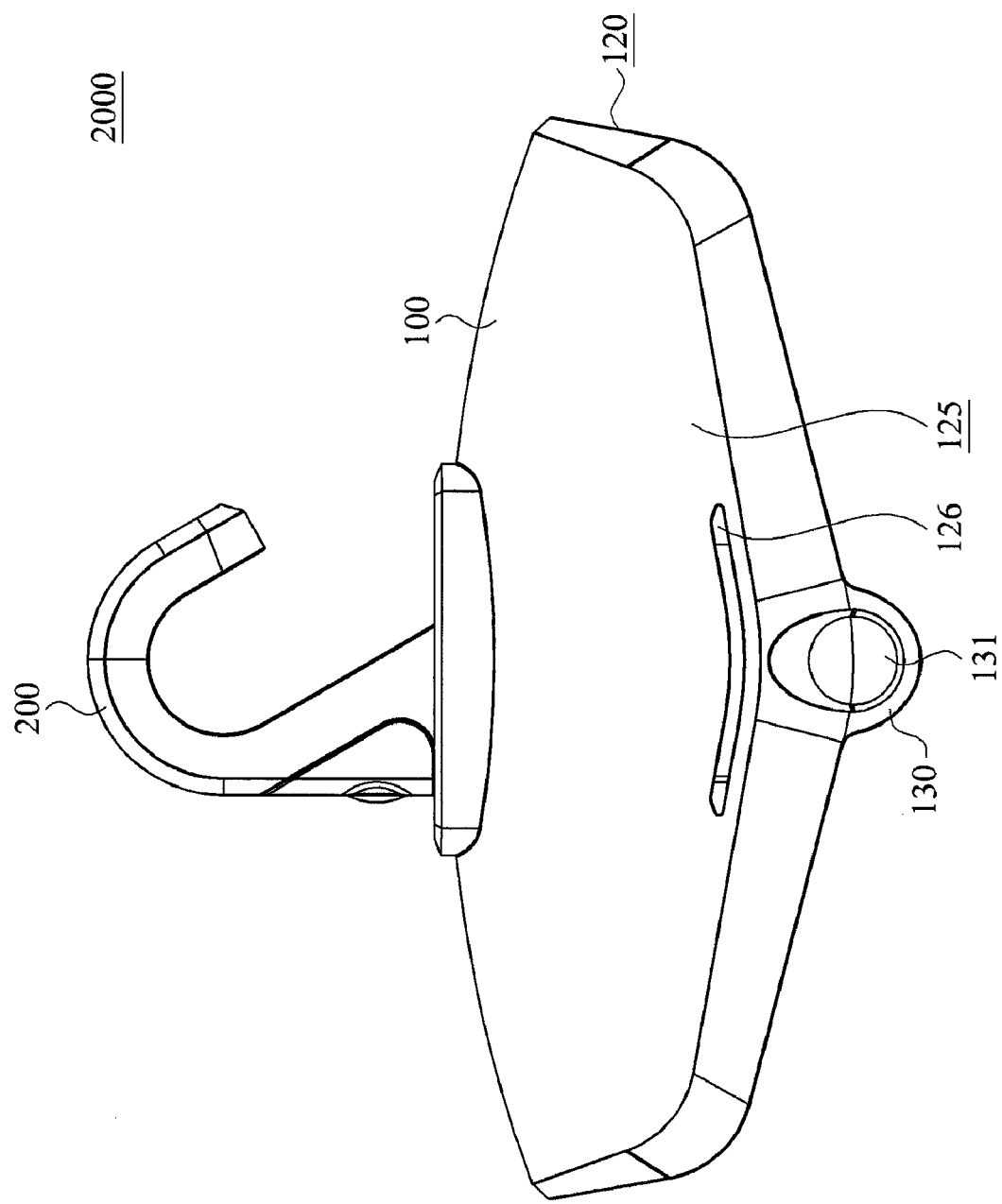
FIG. 2 shows an ozone generator employed in the ozone device of the present invention.
Figure 3:
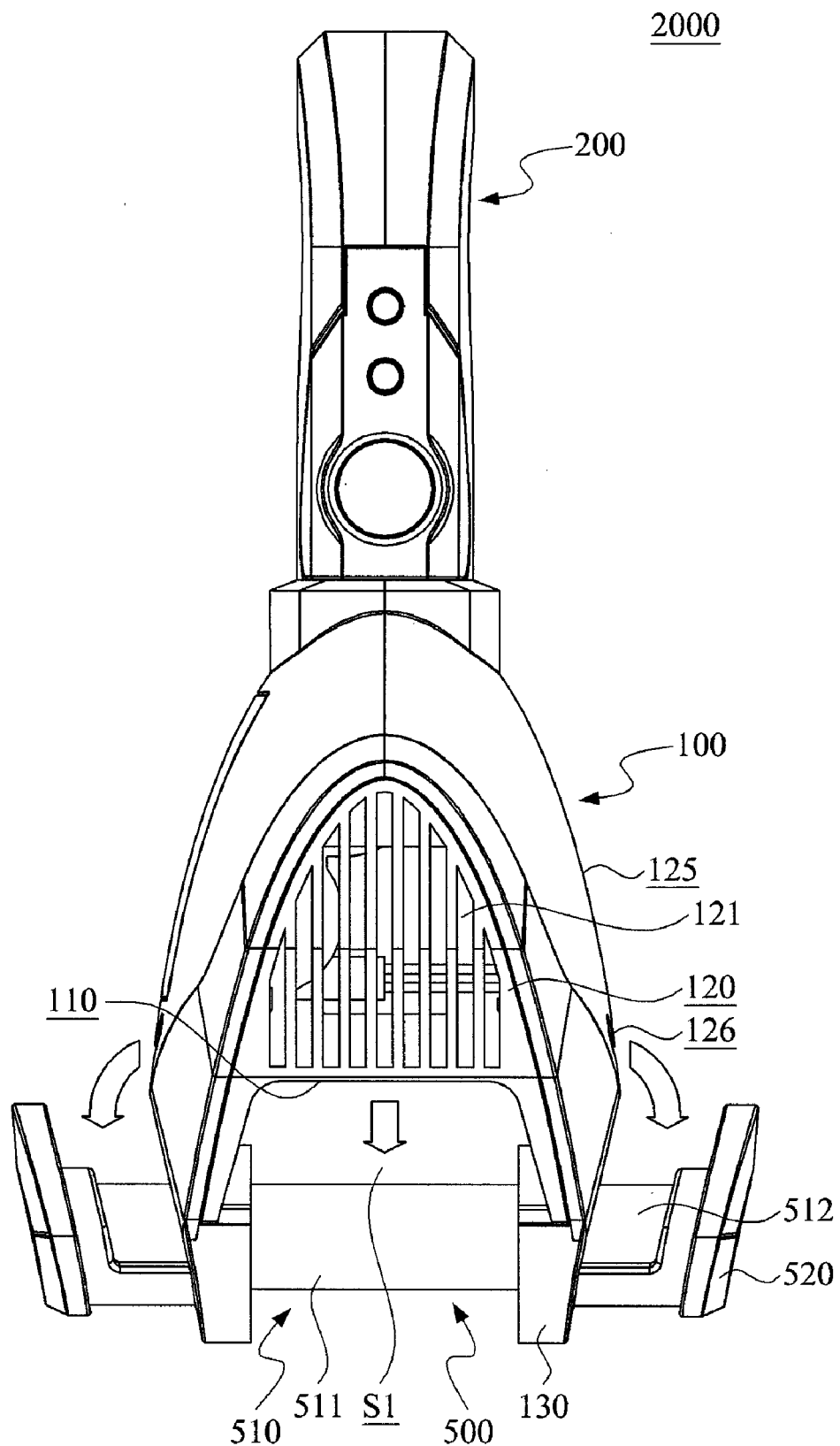
FIG. 3 is a lateral side view of the ozone generator employed in the ozone device of the present invention.
Figure 4:
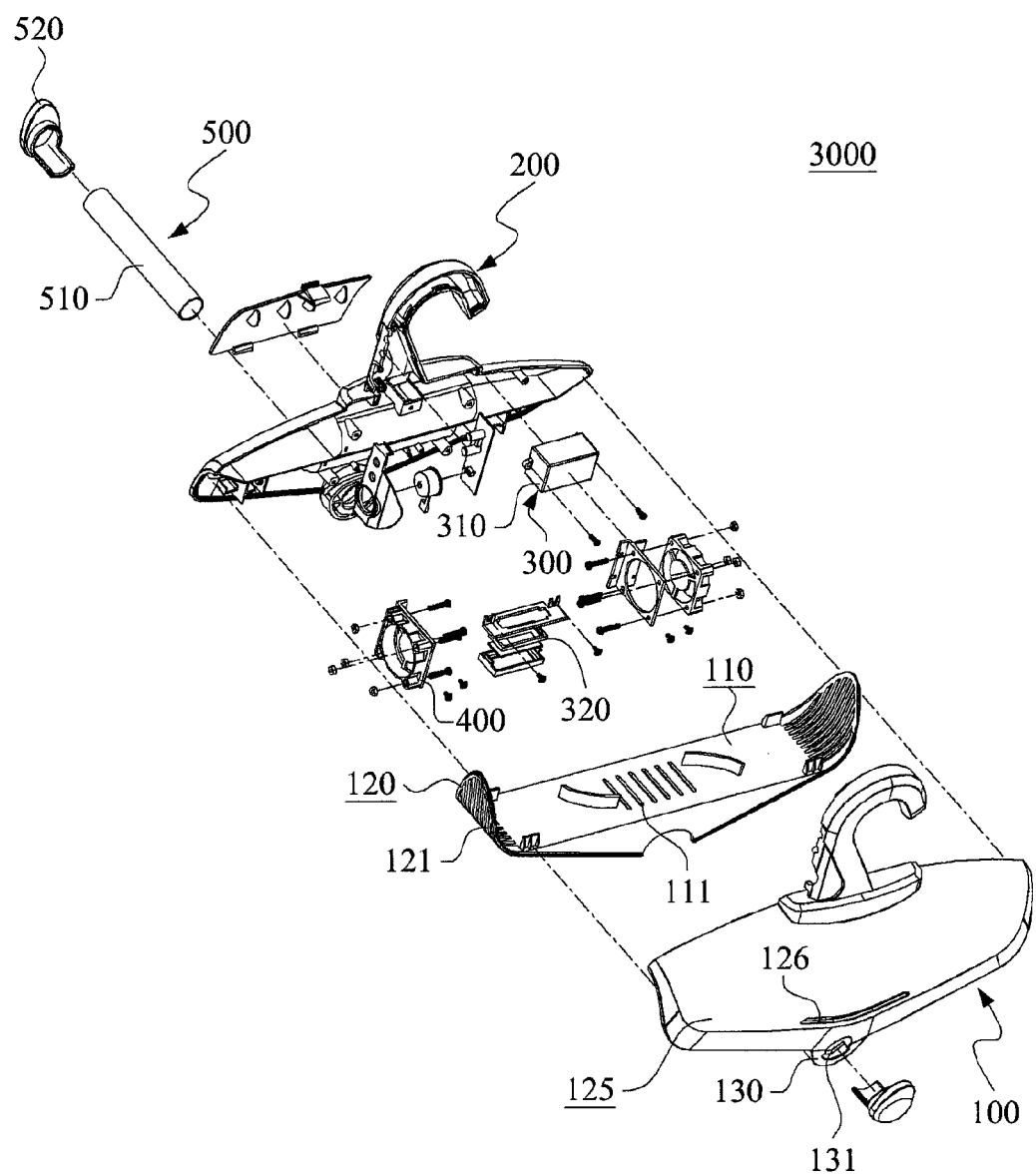
FIG. 4 is an exploded view of the ozone generator shown in FIG. 2.

Referring to FIGS. 2 to 4, wherein FIG. 2 shows the ozone generator 2000 employed in the ozone device 1000 of the present invention, FIG. 3 is a lateral side view of the ozone generator 2000 employed in the ozone device 1000 of the present invention, FIG. 4 is an exploded view of the ozone generator 2000 shown in FIG. 2. As shown, the ozone generator 2000 further includes an ozone producing element 300, two circulating fans 400, and a suspending rod unit 500.

In this embodiment, the casing 100 has one bottom wall 110, front and rear walls 120, and left and right walls 125. The bottom wall 110 is formed with a first ventilation vent 111. Each of front and rear walls 120 is formed with a second ventilation vent 121 while each of the left and right walls 125 is formed with a third ventilation vent 126.

The hanging unit 200, in fact a hook member, is integrally formed with and projects upwardly from the casing 100 and is adapted to be hung detachably onto a suspension member (a rail 4100 within a wardrobe shown in FIG. 7).

The ozone producing element 300 is installed within the casing 100 for generating ozone in order to deodorizing dresses within the garment bag 800. In addition to the dresses, consumer items like shoes and hats, can kept within the garment bag 800 for drying purpose if desired.

The ozone producing element 300 includes an ozone emitter 320 and an ozone controller 310 electrically coupled with the ozone emitter 320. The ozone controller 310 controls supply of electrical power to the ozone emitter 320. The ozone emitter 320 can be a ceramic plate. Since controlling of the ozone controller 310 relative to the ozone emitter 320 is a known art, a detailed description thereof is omitted herein for brevity.

The circulating fans 400 are installed within the casing 100, at two opposite sides of the ozone emitter 320 respectively adjacent to the second ventilation vents 121. In this embodiment, the blow direction of the fans 400 is directed toward the ozone emitter 320 such that the ozone within the casing 100 passes through the first and third ventilation vents 111, 126 and enters into the garment bag 800. Later, the ozone within the garment bag 800 enters into the casing 100 via the second ventilation vents 121. Alternately, the circulating fans 400 can be disposed exterior to the casing 100, respectively adjacent to the first and second ventilation vents 111, 121.

Location of the first, second and third ventilation vents 111, 121, 126 on the casing 100 should not be limited to a specific spot. Any position is possible so long as to permit smooth flow of ozone from the casing 100 into the garment bag 800 and vice versa. For instance, the first ventilation vent 111 is formed through the bottom wall while the second ventilation vents 121 are formed through the lateral side walls of the casing 100. The blown direction of the fans 400 is not restricted to any specific direction so long as the air circulates smoothly within the garment bag 800 will be alright.

The suspending rod unit 500 is fixed to the casing 100, includes a clothe hanger 5000 hung detachably onto the suspension member for carrying the dresses 6000 thereon (see FIG. 7). The suspending rod unit 500 includes an inner suspending rod 510 and two outer suspending rods 520 attached respectively to opposite ends of the inner suspending rod 510.

The casing 100 further has a suspension lug 130 that projects downward from the bottom wall 110 and that is formed with a rod hole 131 for extension of the inner suspending rod 510 when the suspending rod unit 500 is mounted to the lug member 130. Under this condition, the inner suspending rod 510 is disposed below and cooperates with the bottom wall 110 of the casing 10 to define a gap S1 to facilitate passage of the clothe hanger 5000 therethrough and the inner suspending rod 510 itself defines an inner hanging room 511 while the outer suspending rods 520 are disposed exterior to the lug member 130 to define two outer hanging rooms 512.

As illustrated in FIG. 3, in case the clothe hanger 5000 is hung onto the inner or outer hanging room 511, 512, the dresses carried by the hanger 5000 will be deodorized by the ozone emitted from the first ventilation vent 111 while the dresses carried by another clothe hanger on the outer hanging room 512 will be deodorized by the ozone emitted from the third ventilation vents 126. Since the undesired smell is generally contaminated on the external surface of the dresses, and the dresses being exposed to the first and second ventilation vents 111, 121 will be deodorized effectively.

Figure 5:
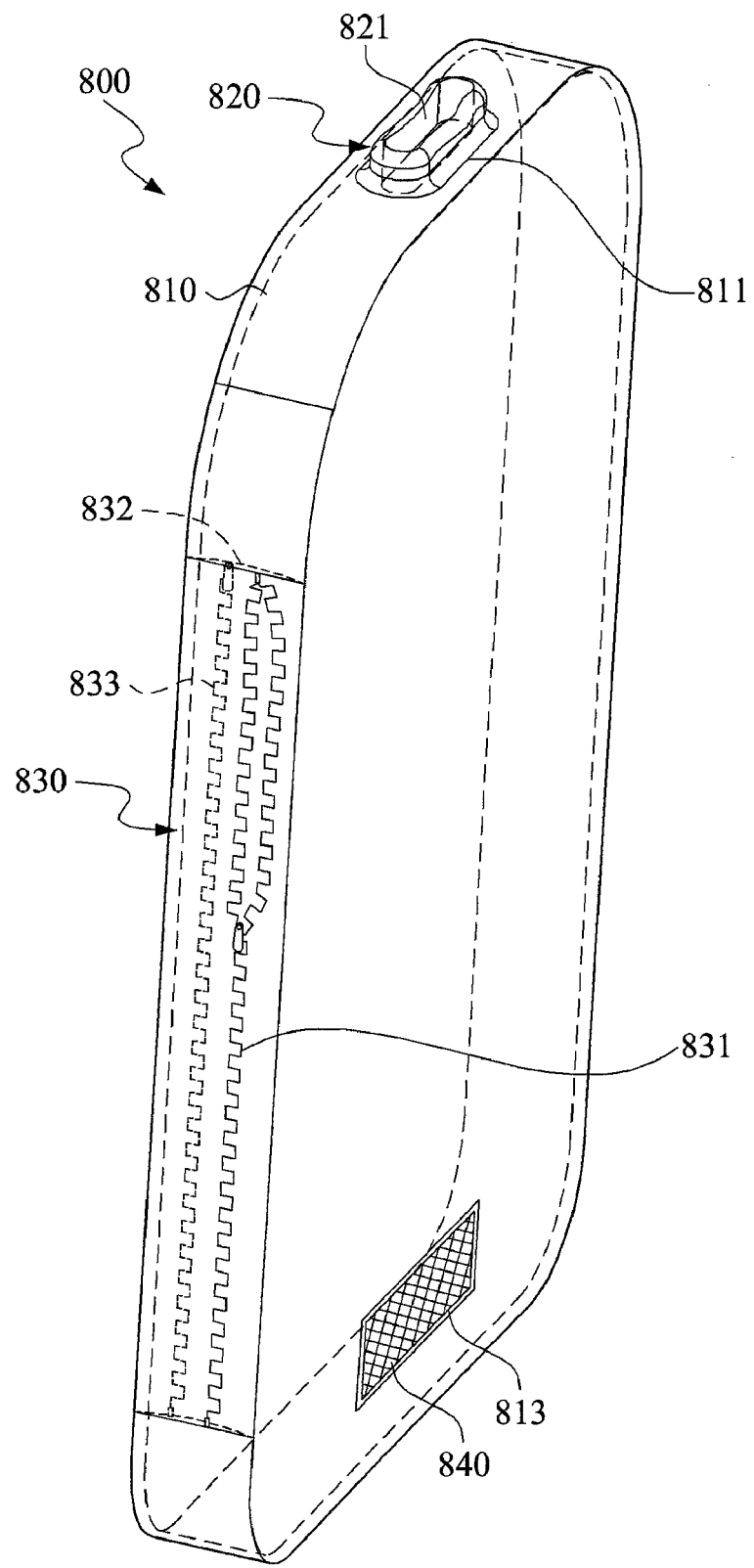
FIG. 5 is a perspective view of a garment bag of the present invention.

Referring to FIGS. 1 and 5, wherein FIG. 5 is a perspective view of a garment bag of the present invention. The garment bag 800 is sleeved over and cooperates with the casing 100 of the ozone generator 2000 to define a chamber so that dresses can be kept therein and the ozone can be circulated therein. The garment bag 800 includes a hollow bag body 810, a seal unit 820, a zipper structure 830 and an ozone filter unit 840. The bag body 810 can be a bending or folding structure. The bag body 810 can be formed by plastics, and can be translucent or transparent. When the bag body 810 is sleeved over the ozone generator 200, the ozone generator 2000 generates the ozone into the inside of the bag body 810. The top side of the bag body 810 has a first or opening 811, and the side of the bag body 810 has a second or opening 813.

The seal unit 820 can be disposed on the first open 811 of the bag body 810 and the seal unit 820 is sleeved over the ozone generator 2000. The seal unit 820 can be a hollow structure. The top of the seal unit 820 has a seal or opening 821, and the seal open 821 can be communicated with the inner side of the bag body 810 via the first open 811.

When the ozone generator 2000 is sleeved over the garment bag 800, the casing 100 of the ozone generator 2000 is disposed within the bag body 810, and the hanging unit 200 projects through the seal open 821 of the seal unit 820. In this time, the inner wall of the seal unit 820 is contacted to the ozone generator 2000. Perfectly, the first open 811 and/or the seal open 821 is contacted to the top side of the casing 100 of the ozone generator 2000 to prevent the ozone generated by the ozone generator 2000 leaking out from the seal open 821. The seal unit 820 can be formed by silicone. Because the characteristic of the silicone is elastic and soft, the ozone generator 2000 is covered by the seal unit 820 completely.

Figure 6:
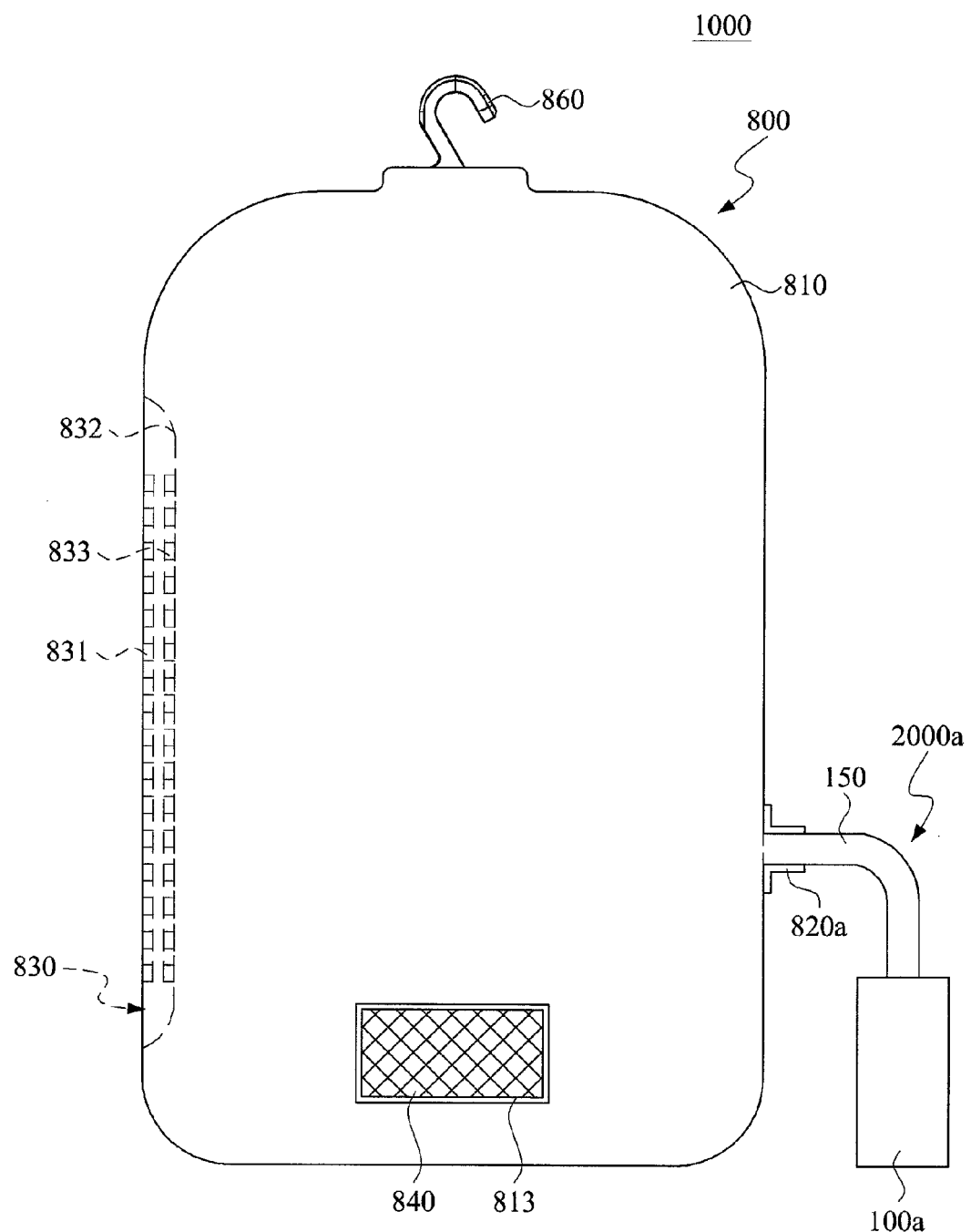
FIG. 6 is a schematic view of the second embodiment of an ozone device of the present invention.

In second embodiment, please refer to FIG. 6, which the ozone generator 2000a is not disposed within the bag body 810. The ozone generator 2000a includes a communication tube 150. One end of the communication tube 150 is connected to the casing 100a of the ozone generator 2000a, and the other end is sleeved over to the seal unit 820a. Therefore, the ozone generated by the ozone generator 2000a is transmitted to the inner side of the bag body 810 of the garment bag 800 via the communication tube 150. The bag body 810 has a hanging element 860 projecting outward from a top portion thereof. The hanging element 860 can be hung on a suspension member, such as the rail 4100 shown in FIG. 7.

Please refer to FIGS. 1 and 5, the zipper structure 830 is disposed on the side of the bag body 810 to prevent the ozone leaking out from the zipper structure 830. The dresses 6000 (shown on FIG. 7) can be hung on the ozone generator 2000 in the bag body 81 via the zipper structure 830.

The zipper structure 830 includes an outer zipper unit 831, an inner separation unit 832 and an inner zipper unit 833. The outer zipper unit 831 is disposed in the side of the bag body 810, and the outer zipper unit 831 can be a zipper. One person skilled in the art knows that one zipper is for fastening an opening for access into the chamber. The zipper can be pulled upward to cover the opening, and downward to uncover the opening.

The material of the inner separation unit 832 can be the same as the bag body 810. The inner separation unit 832 can be a flexural and thin structure. The inner separation unit 832 can be extended from the inner side of the bag body 810 and cover the outer zipper unit 831. The inner separation unit 832 can be integrally formed with the bag body 810 or combined with the bag body 810 with adhesive. The inner zipper unit 833 can be a zipper and is disposed on the inner separation unit 832. The outer zipper unit 831 and the inner zipper unit 833 can be opened, and the dresses 6000 can be hung on the ozone generator 2000 within the bag body 810 via the outer zipper unit 831 and the inner zipper unit 833. In other embodiment, the zipper structure 830 includes only one separation unit.

One person skilled in the art knows that small amount of air or ozone can leak out via the gaps of zipper. Therefore, the zipper structure 830 of the present invention is a double zipper structure. When some ozone leaks to exterior via the inner zipper unit 833, most of the ozone will be blocked by the outer zipper unit 83. Finally, the exterior ozone content is in conformance with ozone safety standard. Especially, shown on FIG. 5, the outer zipper unit 831 and inner zipper unit 833 are and separation to each other. The ozone will not leak out from the inner zipper unit 833 to the outer zipper unit 831 directly, and the leaking amount of ozone will be further decreased.

The ozone filter unit 840 is disposed and covered the second open 813 of the side of the bag body 810.

When the ozone in the bag body 810 flows into the ozone filter unit 840, the ozone will be decomposed by the ozone filter unit 840. The ozone filter unit 840 can be ozone filter gauze. Therefore, the ozone out of the bag body 810 will not get above the ozone safety standard. The ozone filter gauze can be formed by oxide of metal or other catalyst. The specific material of the ozone filter gauze or the theory of the ozone decomposition are prior art, not describe here.

In the present invention, the ozone with odor molecule in the bag body 810 can flow to the ozone filter unit 840 and be decomposed by the ozone filter unit 840, and the air can flow in and out from the bag body 810 via the ozone filter unit 840. Therefore, the decomposition rate of the ozone can be increased, and the odor can be deodorized faster.

FIG. 7 illustrates how the ozone device 1000 of the present invention is used within a wardrobe or cabinet. Also referring to FIG. 4, the wardrobe 400 is provided with a suspension member 4100, upon which the hanging unit 200 can be detachably hooked on. Under this condition, the clothe hanger 5000 with the dresses 6000 can be hooked detachably onto the suspension rod unit 500. Since the garment bag 800 being sleeved over the ozone generator 2000 and when the circulating fans 400 are activated, the ozone from the casing 100 is outputted into the garment bag 800 via the first and third ventilation vents 111, 126 so as to deodorize the smell stained on external surfaces of the dresses 6000 and to attach the odor molecule when the ozone flows along the circulation path P. Later, the ozone flows back into the casing 100 via the second ventilation vents 121. In another embodiment, the dresses 6000 can be hooked directly and detachably on the suspension rod unit 500.

Please refer to FIG. 7, the ozone filter unit 840 can be disposed on the bottom of the side of the bag body 810, because the molecular weight of ozone is heavier than the air, and the ozone flows from the top of the bag body 810 to the bottom. The ozone will flow to the bottom of the bag body 810 and attaches odor molecule from the dresses 6000. Finally, the ozone with the odor molecule flows to the ozone filter unit 840, and the ozone filter unit 840 can decompose the ozone with the odor molecule to increase deodorization efficiency. Besides, the air exterior of the bag body 810 can flow into the bag body 810 via the ozone filter unit 840, and follow the circulation path P to the ozone generator 2000 for generating ozone. The odor molecule can be aroma, stink, cacidrosis or smoke molecule. In another embodiment, the dresses 6000 can be hung on the suspending rod unit 500 directly.

Figure 8:
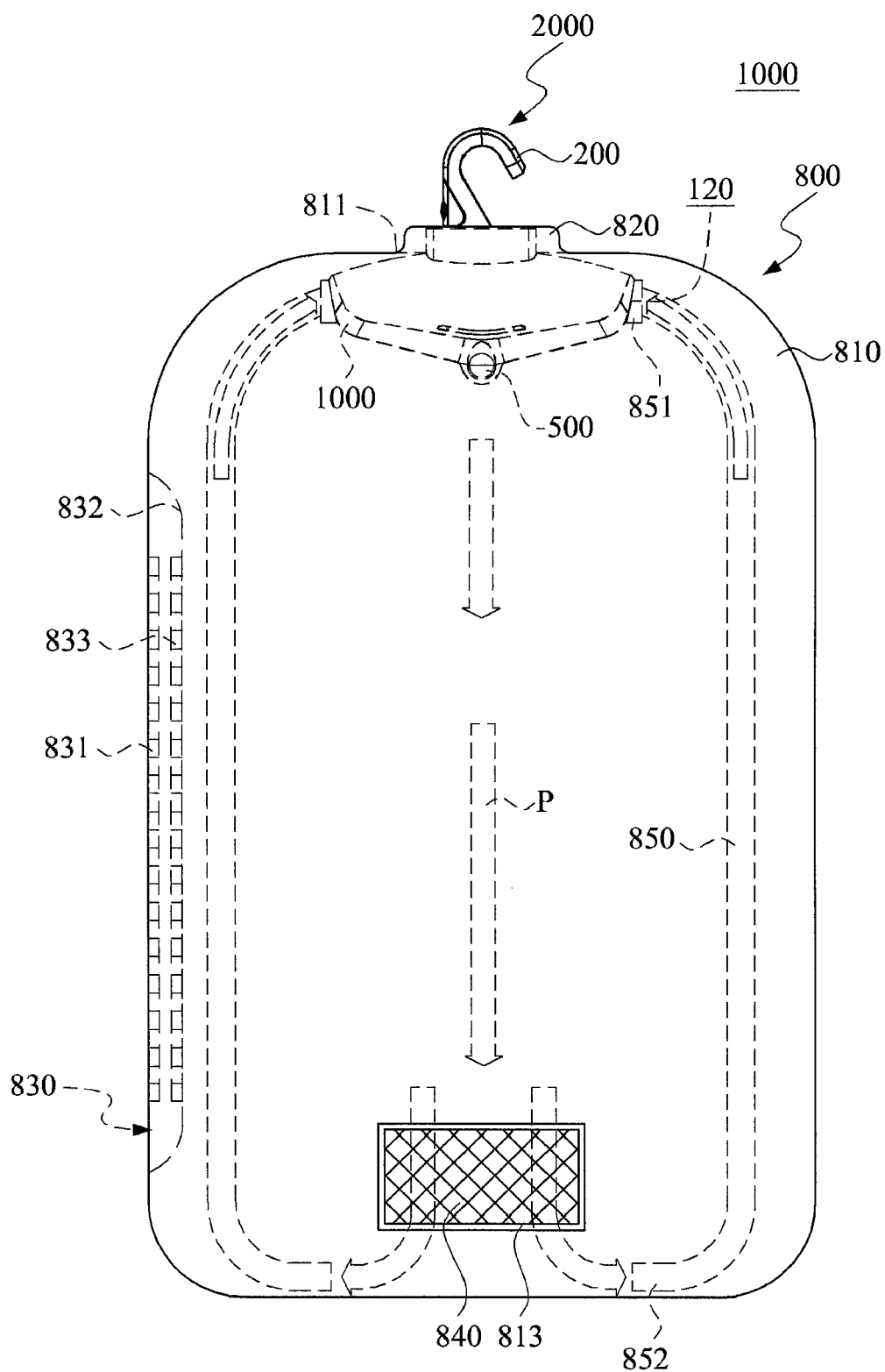
FIG. 8 is a schematic view of the third embodiment of an ozone device of the present invention.

FIG. 8 is a schematic view of the third embodiment of an ozone device of the present invention. Also referring to FIG. 4, the third embodiment has the similar structure as the first embodiment depicted in FIG. 2. The only difference resides in that the garment bag 800 further includes a fluid tube 850 having a first end 3110 connected fluidly to a respective second ventilation vent 121 on the wall 120 and a second end 3120 terminating at a lower portion of the garment bag 800. Alternately, one end of the fluid tube 850 can be connected fluidly to the first or third ventilation vent 111, 126. The restriction should not be limited only thereto.

In the third embodiment shown in FIG. 8, upon activation of the circulating fan 400, the ozone from the casing 100 is outputted into the garment bag 800 via the first and third ventilation vents 111, 126 when the ozone flows along the circulation path P without passing through the second ventilation vents 121. Later, the ozone flows back into the casing 100 via the second end 3120 of the fluid tube 850 and the first end 3110 connected fluidly to the respective second ventilation vent 121 on the wall 120. Since the ozone generated by the ozone generator 2000 circulates within the chamber defined cooperatively by the garment bag 800 and the casing 100 repeatedly, most of the ozone circulates within the garment bag 800 for a relatively long time. In the present invention, the ozone generator 2000 can be controlled to operate for short period of time, but the circulating fan 400 for a longer period of time to circulate the ozone for a relatively long time to deodorize the dress. Thus, the ozone device 1000 of the present invention consumers lesser power source when compared to the prior art ones.

As explained above, the ozone generator of the present invention generates lesser ozone amount when compared to the prior art to deodorize the dresses. The seal unit and the zipper structure are to prevent from leaking to exterior of the garment bag. Moreover, the ozone with odor molecule flowing to the ozone filter unit can be decomposed by the ozone filter unit. Therefore, the deodorization rate of dresses can be increased, and the leakage of the ozone will not exceed the ozone safety standard.

While the invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. An garment bag connected to an ozone generator, comprising:
    a hollow bag body receiving ozone generated by the ozone generator;
    a seal unit disposed on the bag body and sleeved over the ozone generator;
    a zipper structure disposed on the side of the bag body to prevent the ozone leaking; and
    a ozone filter unit disposed on the bag body;
    wherein when the ozone in the bag body flows to the ozone filter unit, the ozone filter unit decomposes part of the ozone; wherein the top side of the bag body has a first opening, the seal unit is disposed on the first opening, the seal unit is a hollow structure and has a seal opening, the seal opening communicates with the first opening, and the inner side of the seal unit is contacted to the ozone generator, the ozone generator includes a hanging unit and a casing, the hanging unit projects upwardly from the casing, the casing is installed within the bag body, the casing is contacted to the first opening, and the hanging unit projects through the seal opening.

2. The garment bag according to claim 1, wherein the seal unit is formed by silicone.

3. The garment bag according to claim 1, wherein the zipper structure includes an outer zipper unit disposed on the side of the bag body, an inner separation unit disposed on the inner side of the bag body and covered the outer zipper unit, and an inner zipper unit disposed on the inner separation unit.

4. The garment bag according to claim 3, wherein the outer zipper unit and the inner zipper unit are separate to each other.

5. The garment bag according to claim 1, wherein the side of the bag body has a second opening covered by the ozone filter unit.

6. The garment bag according to claim 1, wherein the ozone generator further comprises a communication tube, the communication tube is sleeved over the seal unit, the ozone generated by the ozone generator is transmitted into the bag body via the communication tube.

7. The garment bag according to claim 6, further comprising a hanging element projecting outward from a top portion of the bag body.

* * * * *